United States Patent [19]
Scott et al.

[11] Patent Number: 4,523,469
[45] Date of Patent: Jun. 18, 1985

[54] LASER GENERATION OF ULTRASONIC WAVEFORM RECONSTRUCTIONS

[75] Inventors: William R. Scott, Doylestown, Pa.; Charles S. Ih, Newark, Del.

[73] Assignee: The United States of America as represented by the Secretary of the Navy, Washington, D.C.

[21] Appl. No.: 459,073

[22] Filed: Jan. 19, 1983

[51] Int. Cl.³ ............................................. G01N 29/04
[52] U.S. Cl. ...................................... 73/603; 73/643; 73/662
[58] Field of Search .................. 73/603, 655, 656, 657, 73/643, 606, 662; 356/35.5; 350/358

[56] References Cited
U.S. PATENT DOCUMENTS 3,978,713  9/1976  Penney ................................. 73/643
4,246,793  1/1981  Fairand et al. ...................... 73/643
4,422,167  12/1983  Shajenko ............................. 73/655

*Primary Examiner*—Anthony V. Ciarlante
*Attorney, Agent, or Firm*—Robert F. Beers; Henry Hansen

[57] ABSTRACT

A series of pulses are transmitted to a first laser and the same series of pulses through a time delay network to a second laser. Each laser provides pulses of light through separate diagonal mirrors and through respective transparent holograms. Each light beam is then brought into convergence by respective sides of a wedge shaped reflector and brought into spacially coincident focus by an imaging lens onto the surface of a sample under test. The two hologram transparencies are imaged spacially coincident but separated in time on the face of the sample. Thermal elastic waves produced by laser heating at the sample surface transform into a desired acoustic beam pattern determined by the nature of the wavefronts which the hologram transparency represents. The position of the coincident image on the sample may be moved by varying the time between the two pulses.

7 Claims, 1 Drawing Figure

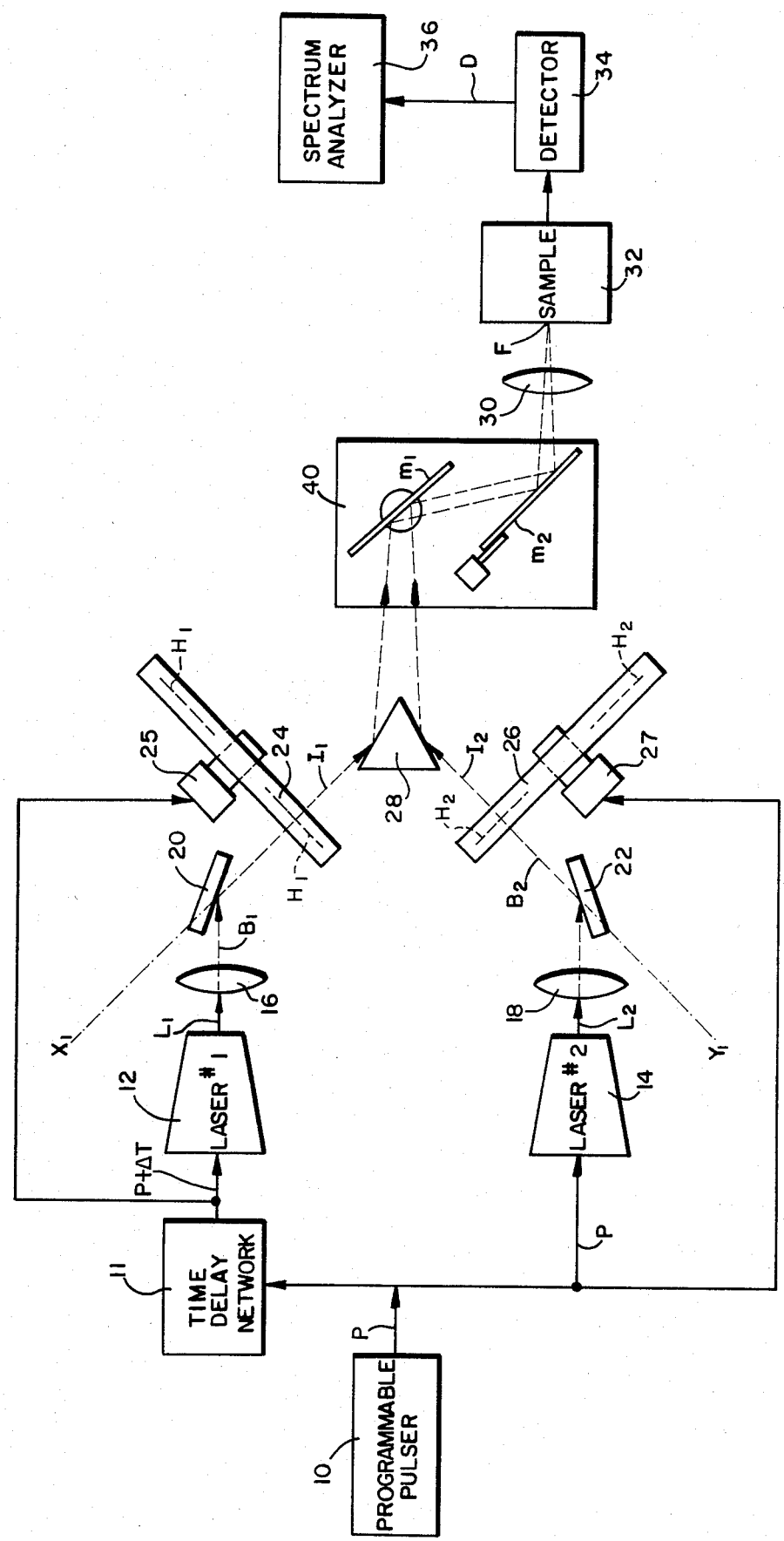

LASER GENERATION OF ULTRASONIC WAVEFORM RECONSTRUCTIONS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Current methods for producing focused or directed ultrasonic stress waves in a sample material involve, in most part, the use of piezoelectric devices. Such devices are used individually, with lenses or in arrays the latter being capable of beam direction by varying the phases of different array elements. The piezoelectric devices provide beam patterns which are difficult to predict and to reproduce.

The array technique creates side lobes which direct a certain portion of the beam in a direction other than that desired. Both the individual piezoelectric devices and array systems require direct physical contact with the sample to couple ultrasonic waves therein. The nature and strength of the contact can have large and unpredictable effects on the waves which are transmitted.

SUMMARY OF THE INVENTION

Accordingly, it is a general purpose of the invention to provide an apparatus to control a beam pattern of laser generated ultrasonic waves through the projection of holographic wavefront images. Another object of the present invention is to provide ultrasonic waves through laser excitation that can be generated remotely from a single or multiple source. A further object of the present invention is to produce ultrasonic waves through laser excitation having continuously variable intensities generated as a function of position by projecting an image in varying gray levels. A still further object of the present invention is to provide a source of ultrasonic excitation that is reproducable and easily characterized. And yet another object of the present invention is to provide ultrasonic waves through laser excitation having uniquely configured beam patterns. Yet a further object of the present invention is to provide an increase in focused power level of an ultrasonic stress wave without causing thermal damage. A still further object of the present invention is to provide direct energy to a given point in a sample medium from an arbitrary angle.

Briefly, these and other objects of the present invention are accomplished by two pulsed lasers each providing pulses of laser light through respective wavefront image transparencies. The two light beams separated in time are brought into spacial convergence and into spacially coincident focus upon the surface of a sample of material for ultrasonic testing thereof.

Other objects, advantages and novel features of the invention become apparent from the following detailed description of the invention when considered in conjunction with the accompanying drawings wherein:

BRIEF DESCRIPTION OF THE DRAWINGS

The one FIGURE is a diagrammatic illustration of an apparatus employed to control the beam pattern of laser generated ultrasonic waves through the projection of holographic wavefront images according to the invention.

DESCRIPTION OF THE PREFERRED EMBODIMENT

Referring to FIG. 1, a programmable pulser 10 of conventional design provides a signal P having pulse characteristics such as pulse amplitude, width $\Delta \tau$ and repetition rate $\omega$ for triggering a laser device of conventional design. A time delay network 11 of conventional design is connected to receive signal P for providing signal $P + \Delta T$ similar to P, but delayed in time. A first laser device 12 of conventional design is connected for receiving signal $(P + \Delta T)$ for triggering emission therefrom of a narrow intense beam of light $L_1$. A first beam expanding telescope 16 is positioned to receive and expand pulsed light wave $L_1$ for providing an approximate one inch diameter beam $B_1$. A first diagonal mirror 20 is positioned to reflect beam $B_1$ along an axis $X_1$. A first hologram transparency H is positioned perpendicular to axis $X_1$ to receive beam $B_1$ for providing a holographic beam $I_1$ comprised of a series of spots and lines whose intensity is a monotonic function of the acoustic field which must be generated at the surface of a sample 32 in order to produce a desired acoustic beam pattern within the sample. For example, an ultrasonic beam focusing to a point directly in front of the sample surface would require a hologram consisting of a series of precisely spaced concentric annular rings. A second laser device 14 of conventional design is connected to receive signal P from programmable pulser 10 for triggering the emission therefrom of a second narrow intense wave of light $L_2$. A second beam expanding telescope 18 is positioned to receive and expand light wave $L_2$ for providing an approximate one inch diameter beam $B_2$. A second diagonal mirror 22 is positioned to reflect beam $B_2$ onto an axis $Y_1$. A second hologram transparency $H_2$ is positioned perpendicular to axis $Y_1$ to receive beam $B_2$ for providing a second holographic beam $I_2$ comprised of a series of spots and lines whose intensity is a monotonic function of the acoustic field which must be generated at the surface of the sample 32 in order to produce a desired acoustic beam pattern within the sample. For example, an ultrasonic beam focusing to a point directly in front of the sample surface would require a hologram consisting of a series of precisely spaced concentric annular rings. A plurality of hologram transparencies $H_1$ and $H_2$ are held in place in an independent bin by magazine loaders 24, 26 synchronously rotated by motors 25, 27 by pulses $P + \Delta T$ and P respectively for changing the holograms thereby changing the images for the purpose of localized scanning of the ultrasonic beam generated on the surface of sample 32. A wedge 28 tapering from a thick back to a thin edge having reflective sides is positioned to reflect holographic beam $I_1$ from a first reflective side and holographic beam $I_2$ from a second reflective side into a scanner 40 for moving the beams $B_1$ and $B_2$ onto various locations on sample 32 in a regular pattern such as a raster. A number of commercial devices consisting of rotating mirrors acousto optic modulators or other means for deviating beams already exist. The means shown in FIG. 1 consist of two rotating mirrors M1 and M2. M1 consists of a mirror rotating on axis Z1 perpendicular to the page deflecting the beams $B_1$ and $B_2$ in the plane of the page while $M_2$ consists of a similar mirror with rotating axis Z2 in the plane of the page and deflecting the beams B1 and B2 perpendicular to the plane of the page. The two deflections allow any point F on the surface of the sample 32 to serve as a target for the beams. After leaving the scanner 40, the beam $B_1$ and $B_2$ pass through lens 30 which causes them to converge and form images $I_1$ and $I_2$ on the surface of sample 32 at any point F targeted by the scanner. Holographic images from holographic beams 1 and 2 incident upon sample 32 are of sufficient intensity and have a sufficiently short rise time, (5 to 50 ns typically) to produce a detectable ultrasonic excitation therein. By varying the time delay, pulse duration and shape of pulse P, different ultrasonic waveforms can be produced to interact with sample 32. A detector 34 of conventional design comprising a piezoelectric sensor is physically connected to sample 32 for providing a signal D consisting of a voltage fluctuation characteristic of the ultrasonic waves produced at sample 32. The ultrasonic waves provide information indicative of the internal structure of the sample 32 and any defects therein. A spectrum analyzer 36 is connected to receive and process signal D thereby providing information relating to the location of various defects within sample 32. Different frequency components of signal D will be representative of ultrasonic waves which left the sample surface at different angles in much the same way that different frequencies of light are deflected from a diffraction grating at different angle. In this way, waves with different frequencies will interrogate different portions of sample 32.

The nature of the wave motions and beam patterns produced in sample 32 is a function of the type of excitation, the frequency and the composition of sample 32 and is best understood in terms of stress wave boundry value problems, For purposes of understanding the invention, the problem is illustrated by an example utilizing a single frequency wave W in a liquid medium. Since such a wave is time harmonic, its amplitude at any time t, when specified over a plane, is sufficient to determine its behavior for all time and space. In general, any type of wave motion can be described as a superposition of many frequencies. Plus, if one imposes the conditions for a particular type of wave motion upon some plane in a medium, that motion will be realized within the medium and each of its Fourier components will separately exhibit its own independent mode propogation. The following example illustrates how the laser generated ultrasonic wave reconstruction is applied to generating a particular type of wave motion such as a plane wave in a fluid.

For simplicity, assume that sample 32 is replaced by a black optically absorbing thin metal sheet M in a fluid medium F1 and that the two pulsed laser beams $B_1$ and $B_2$ passing through lens 30 are focused onto the plane of sheet M. Let us further assume that the image $I_1$ of the hologram $H_1$ may be described as a one dimensional spacial light intensity variation in $B_1$ of the above form $$I(x) = (\cos(kx))^{1/2} \qquad (1)$$

Here the X direction is vertical and k is a constant when focused onto the metal plane M. This will thermoelastically generate acoustic waves at the surface of the metal plane whose spacial amplitude will vary as $$A(x) = \cos kx \qquad (2)$$

Similarly the lower beam $B_2$ passing through hologram 26 will produce an acoustic wave with spacial amplitude variation of the form $$A(x) = A_o \sin kx \qquad (3)$$

In general, the thermoelastic waves generated by light pulses have a continuous spectrum of frequency components whose peak intensity is in the range $f = 1/t$ where t is the rise time of the light pulse.

If the spectrum analyzer 36 is tuned to a particular frequency $f_1$ so that only the portion of the detected signal lying at that frequency is monitored, then the spacial variation of this component of the acoustic signal within the fluid medium will be exactly the same as if the light beams $B_1$ and $B_2$ were modulated at the frequency $f_1$. $f_1$ is not the electromagnetic frequency of the light ($10^{14}$ Hz) but the frequency of the desired acoustic wave ($10^6$–$10^7$ Hz). If we account for the fact that there is a time delay $\Delta T$ between beams $B_1$ and $B_2$, the resulting amplitude developed at the plane M will be of the form $$A(x) = A_o(\cos kx \cos(w_1 t) + \sin kx (\cos w(t + \Delta T))) \qquad (4)$$

where $W_1 = 2\pi f_1$. Letting $$\Delta T W = \pi/2 \qquad (5)$$

by adjusting the time delay $$A(x) = A(\cos kx \cos W \cdot t + \sin kx \sin Wt) = \cos(Wt - kx) \qquad (6)$$

This is exactly the boundary condition corresponding to a plane acoustic wave of frequency f. and wavelength $\lambda_1$ leaving the surface of the plane M at an angle $\theta = \arcsin k \lambda/2 \pi$. Where $\lambda_1 = C/f_1$, C being the velocity of sound in the fluid medium F.

The angle $\theta$ can be varied by adjusting $f_1$ and $\Delta T$ to satisfy condition (5) above. Thus a virtual plane wave at any given angle may be launched into the fluid medium. Such waves can interact with discontinuities in the medium thereby indicating the presence of such discontinuities.

The above example is a simplified example of using the holographic technique to control beam patterns and clearly many other types of beam patterns may be created by varying the nature of the holograms and the length of the time delay.

In operation, programmable pulser 10 provides pulses to laser device 14 and through time delay network 11 to laser device 12. Laser devices 12 and 14, provide light waves $L_1$ and $L_2$ through beam expanders 16 and 18 respectively. Beams $B_1$ and $B_2$ are reflected from diagonal mirrors 20 and 22 respectively and onto axes $X_1$ and $Y_1$ through wavefront image transparencies $H_1$ and $H_2$ respectively. Images $I_1$ and $I_2$ are reflected from the opposite sides of wedge 28 to converge through imaging lens 30 which focuses image $I_1$ and $I_2$ upon the surface or sample 32.

Some of the many advantages of the present invention can now be readily apparent. The invention provides for the capability of generating ultrasonic waves remotely from a single or multiple source. Additionally, the invention permits analytical characterization of beam patterns that can be faithfully reproduced with each use. The invention provides for an increase in focus power level below damage threshold for laser transduction, since laser energy is distributed on the surface of a sample and not focused on a spot on the sample surface. Further, the invention has the ability to direct energy to a given point within a sample from an arbitrary angle which is important in the determination of defect geometry in structural materials. The use of two alternating beams $B_1$ and $B_2$ projecting time separated images has an advantage over a single beam in that it diminishes side lobes in the acoustic beam by allowing better matching to the time dependent boundary conditions needed to produce an obliquely directed beam going in a single direction. The use of light beams to generate and receive acoustic waves has the further advantage that the signals transmitted over these beams are not readily subject to electromagnetic interference or other types of mechanical interference which would occur if acoustic waves were brought directly through liquid medium onto the sample surface.

Obviously, many modifications and variations of the present invention are possible in view of the above teachings. It is therefore to be understood that within the scope of the appended claims the invention may be practiced otherwise than is specifically described.

What is claimed is:

1. Apparatus for nondestructive testing of a material by ultrasonic signal reconstructions comprising:
   a signal generator for providing pulses of programmable width, rise time, amplitude and repetition rate;
   first laser means connected to receive the pulse for providing a first holographic beam;
   second laser means connected to receive the pulses for providing a second holographic beam, the first beam being delayed a predetermined increment of time after the second beam;
   focus means positioned to receive the first and second beams for producing a coincident image of the first and second beams on the surface of the material; and
   output means positioned to detect the ultrasonic signal eminating from the material in response to the image and provide a frequency spectrum of the signal indicative of the defect geometry of the material.

2. Apparatus according to claim 1 wherein said first laser means comprises:
   a time delay network connected to receive the pulses for producing delayed pulses for delaying the first beam.

3. Apparatus according to claim 2 wherein:
   said first laser means includes a first laser device connected to be triggered by the delayed pulses for providing a narrow emission, a first optic means positioned to diffuse and reflect the emission on a first predetermined axis, and holographic means positioned along said first axis for selectably providing the first holographic beam; and
   said second laser means includes a second laser device connected to be triggered by the pulses for providing a narrow laser emission, a second optic means positioned to diffuse and reflect the emission on a second predetermined axis, and holographic means positioned along said second axis for selectably providing the second holographic beam.

4. Apparatus of claim 3 wherein:
   said first holographic means includes a rotatable loader for storing a first plurality of hologram transparencies each located in an independent bin of said loader for positioning said individual transparencies perpendicular to the respective axis, and a motor connected to receive the delayed pulses for synchronously rotating said loader; and
   said second holographic means includes a rotatable loader for storing a second plurality of hologram transparencies each located in an independent bin of said loader for positioning said individual transparencies perpendicular to the respective axis, and a motor connected to receive the pulses for synchronously rotating said loader.

5. Apparatus of claim 4 wherein said focus means comprises:
   a dual reflector positioned to simultaneously reflect the first and second beams;
   third optic means positioned to receive the reflected first and second beams and focus the coincident image thereof on the surface of the material.

6. Apparatus according to claim 5 wherein said dual reflector comprises:
   a rotatable reflector for sweeping said coincident image across the surface of the material.

7. Apparatus according to claim 1 wherein said output means comprises:
   detector means positioned to receive the ultrasonic signal for producing an output indicative thereof; and
   display means connected to receive the detector means output for producing the frequency spectrum.

* * * * *